(12) United States Patent
Pazenok et al.

(10) Patent No.: US 8,350,053 B2
(45) Date of Patent: Jan. 8, 2013

(54) PROCESS FOR THE REGIOSELECTIVE PREPARATION OF 1-ALKYL-3-HALOALKYLPYRAZOLE-4-CARBOXYLIC ACID DERIVATIVES

(75) Inventors: Sergii Pazenok, Solingen (DE); Norbert Lui, Odenthal (DE); Arnd Neeff, Burscheid (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/921,719

(22) PCT Filed: Feb. 26, 2009

(86) PCT No.: PCT/EP2009/001354
§ 371 (c)(1),
(2), (4) Date: Sep. 9, 2010

(87) PCT Pub. No.: WO2009/112157
PCT Pub. Date: Sep. 17, 2009

(65) Prior Publication Data
US 2011/0028735 A1    Feb. 3, 2011

(30) Foreign Application Priority Data
Mar. 10, 2008 (EP) .................... 08152532

(51) Int. Cl.
*C07D 231/10* (2006.01)
(52) U.S. Cl. .................................. 548/374.1
(58) Field of Classification Search ........... None
See application file for complete search history.

(56) References Cited

U.S. PATENT DOCUMENTS

| 7,038,057 | B2 | 5/2006 | Annis et al. | |
| 8,115,012 | B2 * | 2/2012 | Sukopp et al. | 548/374.1 |
| 2006/0116414 | A1 | 6/2006 | Dunkel et al. | |
| 2006/0252944 | A1 | 11/2006 | Lantzsch et al. | |
| 2008/0108686 | A1 | 5/2008 | Gewehr et al. | |
| 2008/0154045 | A1 | 6/2008 | Aihara et al. | |
| 2009/0326242 | A1 | 12/2009 | Pazenok et al. | |
| 2011/0009642 | A1 * | 1/2011 | Pazenok | 548/374.1 |

FOREIGN PATENT DOCUMENTS
EP  1 854 788 A1  11/2007

OTHER PUBLICATIONS

Bonacorso, H.G. et al., "Trifluoroacetylation of unsymmetrical ketone acetals. A convenient route to obtain alkyl side chain trifluromethylated heterocycles," *J. Fluor. Chem.* 99:177-182, Elsevier Science S.A., United States (1999).
International Search Report for International Patent Application No. PCT/EP2009/001354, European Patent Office, Rijswijk, Netherlands, mailed on Apr. 9, 2009.
Office Action mailed Mar. 14, 2011, in U.S. Appl. No. 12/842,243, Pazenok et al., filed Jul. 23, 2010.
Office Action mailed Oct. 20, 2011, in U.S. Appl. No. 12/842,243, Pazenok et al., filed Jul. 23, 2010.

* cited by examiner

*Primary Examiner* — Sun Jae Loewe
(74) *Attorney, Agent, or Firm* — Sterne, Kessler, Goldstein & Fox P.L.L.C.

(57) ABSTRACT

The present invention relates to a process for the regioselective synthesis of 1-alkyl-3-halo-alkylpyrazole-4-carboxylic acid derivatives by cyclization of 2,3-disubstituted acrylic acid derivatives with hydrazines in the presence of carbonyl compounds.

5 Claims, No Drawings

PROCESS FOR THE REGIOSELECTIVE PREPARATION OF 1-ALKYL-3-HALOALKYLPYRAZOLE-4-CARBOXYLIC ACID DERIVATIVES

The present invention relates to a process for the regioselective synthesis of 1-alkyl-3-halo-alkylpyrazole-4-carboxylic acid derivatives by cyclization of 2,3-disubstituted acrylic acid derivatives with hydrazines in the presence of carbonyl compounds.

2-Dihaloacyl-3-dialkylaminoacrylic esters of the formula II (Y=COOAlk, Z=O) are useful intet mediates for the preparation of dihalomethyl-substituted pyrazolylcarboxylic acid derivatives which can be used as precursors of fungicidally active compounds (cf. WO 03/070705).

Pyrazolecarboxylic acid derivatives are usually prepared by reacting acrylic acid derivatives having two leaving groups (Z and A) with hydrazines.

The reaction with the monoalkylhydrazines gives mainly 1-alkylpyrazoles. However, the cyclization is frequently not regioselective. As a consequence, depending on the substrate and the reaction conditions, the unwanted 5-alkylpyrazoles are formed in amounts between 10 and 80% (see Scheme 1).

Scheme 1

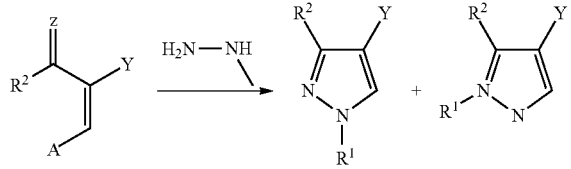

The synthesis of 1-alkylpyrazolecarboxylic acid derivatives by alkylation of pyrazole derivatives unsubstituted in the 1-position frequently also proceeds with formation of both regioisomers (see Scheme 2).

Scheme 2

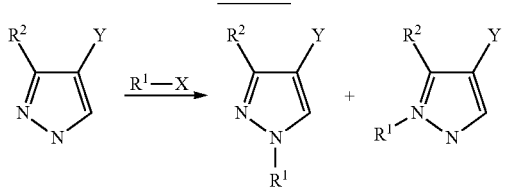

An alternative route of preparing fluorohaloalkylpyrazole-carboxylic acids is the cyclization of, for example, 4,4-dichloro-2-[(dimethylamino)methylidene]-3-oxobutanoate with alkyl-hydrazines followed by a halogen exchange.

WO 2005/042468 discloses a process for preparing 2-dihaloacyl-3-aminoacrylic esters by reacting acid halides with dialkylaminoacrylic esters, followed by their cyclization with alkylhydrazines.

The European patent application No. 07117232.4, hitherto unpublished, describes a process for preparing HCl-free 2-dihaloacyl-3-aminoacrylic esters by reacting acid fluorides with dialkyl-aminoacrylic acid derivatives. The process can be carried out in the absence of a base, as a result of which the removal of halide salts is not required.

WO 2008/022777 describes a process for preparing 3-dihalomethylpyrazole-4-carboxylic acid derivatives by reacting α,α-fluoroamines in the presence of Lewis acids with acrylic acid derivatives, followed by their reaction with alkylhydrazines.

WO 2006/090778 discloses a process for preparing 1-methyl-3-difluoromethylpyrazole-carboxylic esters by cyclization of 2-alkoxymethylenefluoroacylacetate with methylhydrazine in the presence of water and a base. The reaction was carried out in the presence of NaOH or KOH although under these strongly alkaline conditions there is also partial hydrolysis of the COOEt group of the pyrazole ring.

However, the processes above-described all have the disadvantage that the cyclization, even at low temperatures, proceeds only with unsatisfactory regioselectivity.

In view of the prior art described above, it is an object of the present invention to provide a process which does not have the disadvantages mentioned above, thus providing regioselective access to 1-alkyl-3-haloalkylpyrazole-4-carboxylic acid derivatives.

The object described above was achieved by a process for preparing 1-alkyl-3-haloalkyl-pyrazole-4-carboxylic acid derivatives of the formula (I)

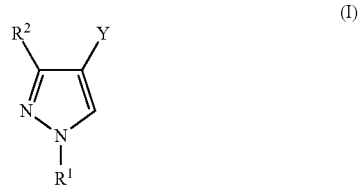

in which
$R^1$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{2-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;
$R^2$ is selected from $C_1$-$C_4$-alkyl groups which may be substituted by one, two or three halogen atoms selected from the group consisting of F, Cl and Br or by a $CF_3$ group;
Y is selected from the group consisting of (C=O)OR$^3$, CN and (C=O)NR$^4$R$^5$, where R$^3$, R$^4$ and R$^5$ independently of one another are selected from the group consisting of hydrogen, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-aryl-alkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;
or where R$^4$ and R$^5$ together with the nitrogen atom to which they are attached may form a 5- or 6-membered ring;
comprising the reaction of a 2-acylated acrylic acid derivative of the formula (II),

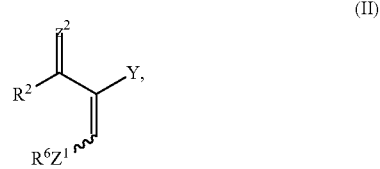

in which $Z^1$ and $Z^2$ independently of one another are selected from the group consisting of O and S, $R^6$ is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;

with an N-alkylhydrazine of the formula (III)

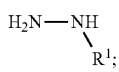

(III)

in the presence of a compound of the formula (IV)

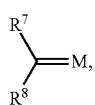

(IV)

in which $R^7$, $R^8$ independently of one another are selected from the group consisting of H, $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group; and M is selected from the group consisting of O, S, Se, NH, NR' and OR', where R' has the meanings defined above.

Surprisingly, under the conditions according to the invention, the 1-alkyl-3-haloalkyl-pyrazole-4-carboxylic acid derivatives of the formula (I) can be prepared with good yields, regioselectivities and in high purity, the process according to the invention, represented in scheme 3, thus overcoming the disadvantages mentioned above of the preparation processes described in the prior art.

Scheme 3

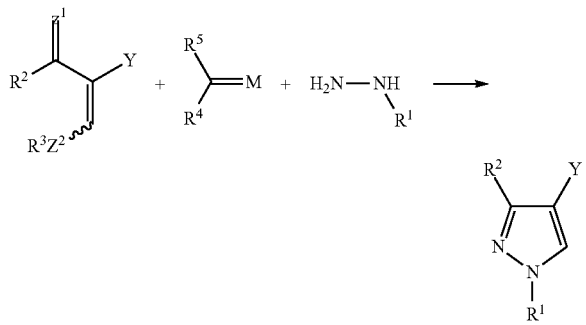

General Definitions

In the context of the present invention, the term halogens (X) comprises, unless defined otherwise, elements selected from the group consisting of fluorine, chlorine, bromine and iodine, where fluorine, chlorine and bromine are used with preference and fluorine and chlorine with particular preference.

Optionally substituted groups may be mono- or polysubstituted, where in the case of polysubstitution the substituents may be identical or different.

Alkyl groups substituted by one or more halogen atoms (—X) are, for example, selected from the group consisting of trifluoromethyl($CF_3$), difluoromethyl($CHF_2$), $CF_3CH_2$, $ClCH_2$, $CF_3CCl_2$.

In the context of the present invention, unless defined otherwise, alkyl groups are straight-chain or branched hydrocarbon groups which may optionally have one, two or more heteroatoms selected from the group consisting of O, N, P and S. Moreover, the alkyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may have one or more heteroatoms selected from the group consisting of N, O, P and S.

In the context of the present invention, cycloalkyl groups are, unless defined otherwise, monocyclic saturated hydrocarbon groups having 3 to 8 carbon ring members, which groups may optionally contain one, two or more heteroatoms selected from the group consisting of O, N, P and S. Moreover, the cycloalkyl groups according to the invention may optionally be substituted by further groups selected from the group consisting of —R', halogen (—X), alkoxy (—OR'), thioether or mercapto (—SR'), amino-(—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopropyl, cyclobutyl, cyclopentyl and cyclohexyl.

The definition $C_1$-$C_{12}$-alkyl comprises the largest range defined herein for an alkyl group. Specifically, this definition comprises, for example, the meanings methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, alkenyl groups are, unless defined otherwise, straight-chain or branched hydrocarbon groups which contain at least one single unsaturation (double bond) and may optionally have one, two or more single or double unsaturations or one, two or more heteroatoms selected from the group consisting of O, N, P and S. Moreover, the alkenyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_2$-$C_{12}$-alkenyl comprises the largest range defined herein for an alkenyl group. Specifically, this definition comprises, for example, the meanings vinyl; allyl (2-propenyl), isopropenyl (1-methylethenyl); but-1-enyl(crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

In the context of the present invention, cycloalkenyl groups are, unless defined otherwise, monocyclic nonaromatic hydrocarbon groups having 3 to 8 carbon ring members and at least one double bond, which groups may optionally contain one, two or more heteroatoms selected from the group consisting of O, N, P and S. Moreover, the cycloalkenyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

Specifically, this definition comprises, for example, the meanings cyclopenten-1-yl, cyclohexen-1-yl, cyclohepta-1,3-dien-1-yl.

In the context of the present invention, alkynyl groups are, unless defined otherwise, straight-chain, branched or cyclic hydrocarbon groups which contain at least one double unsaturation (triple bond) and may optionally have one, two or more single or double unsaturations or one, two or more heteroatoms selected from the group consisting of O, N, P and S. Moreover, the alkynyl groups according to the invention may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a straight-chain, branched or cyclic $C_{1-12}$-alkyl group which may contain one or more heteroatoms selected from the group consisting of N, O, P and S.

The definition $C_2$-$C_{12}$-alkynyl comprises the largest range defined herein for an alkynyl group. Specifically, this definition comprises, for example, the meanings ethynyl(acetylenyl); prop-1-inyl and prop-2-inyl.

In the context of the present invention, aryl groups are, unless defined otherwise, aromatic hydrocarbon groups which may contain one, two or more heteroatoms selected from the group consisting of O, N, P and S and which may optionally be substituted by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms, selected from the group consisting of N, O, P and S.

The definition $C_{5-18}$-aryl comprises the largest range defined herein for an aryl groups having 5 to 18 skeleton atoms, where the carbon atoms may be replaced by heteroatoms. Specifically, this definition comprises, for example, the meanings cyclopentadienyl, phenyl, cyclohepta-trienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, arylalkyl groups (aralkyl groups) are, unless defined otherwise, alkyl groups which are substituted by aryl groups, which may have a $C_{1-8}$-alkylene chain and which may be substituted in the aryl skeleton or the alkylene chain by one or more heteroatoms selected from the group consisting of O, N, P and S and optionally by further groups selected from the group consisting of —R', halogen-(—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-aralkyl group comprises the largest range defined herein for an arylalkyl group having a total of 7 to 19 atoms in the skeleton and the alkylene chain. Specifically, this definition comprises, for example, the meanings benzyl and phenylethyl.

In the context of the present invention, alkylaryl groups (alkaryl groups) are, unless defined otherwise, aryl groups which are substituted by alkyl groups, which may have a $C_{1-8}$-alkylene chain and which may be substituted in the aryl skeleton or the alkylene chain by one or more heteroatoms selected from the groups consisting of O, N, P and S and optionally by further groups selected from the group consisting of —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, where R' is hydrogen or a $C_{1-12}$-alkyl group, preferably a $C_{2-10}$-alkyl group, particularly preferably a $C_{3-8}$-alkyl group, which may contain one or more heteroatoms selected from the group consisting of N, O, P and S.

The definition $C_{7-19}$-alkylaryl group comprises the largest range defined herein for an alkylaryl group having a total of 7 to 19 atoms in the skeleton and the alkylene chain. Specifically, this definition comprises, for example, the meanings tolyl, 2,3-, 2,4-, 2,5-, 2,6-, 3,4- or 3,5-dimethylphenyl.

The alkyl, alkenyl, alkynyl, aryl, alkaryl and aralkyl groups may furthermore contain one or more heteroatoms which—unless defined otherwise—are selected from the group consisting of N, O, P and S. Here, the heteroatoms replace the carbon atoms specified.

If appropriate, the compounds according to the invention can be present as mixtures of various possible isomeric forms, in particular of stereoisomers, such as, for example, E and Z, threo and erythro and also optical isomers, and, if appropriate, also of tautomers. What is disclosed and claimed are both the E and the Z isomers, and also the threo and erythro isomers and the optical isomers, any mixtures of these isomers, and also the possible tautomeric forms.

The 1-alkyl-3-haloalkylpyrazole-4-carboxylic acid derivatives obtainable by the process according to the invention are compounds of the formula (I)

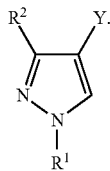
(I)

According to the invention, the radicals in formula (I) have the meanings below:
is selected from the group consisting of $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;
$R^2$ is selected from $C_1$-$C_4$-alkyl groups which may be substituted by one, two or three halogen atoms selected from the group consisting of F, Cl and Br or by a $CF_3$ group;
Y is selected from the group consisting of (C=O)OR$^3$, CN and (C=O)NR$^4$R$^5$, where R$^3$, R$^4$ and R$^5$ independently of one another are selected from the group consisting of $C_{1-12}$-alkyl, $C_{3-8}$-cycloalkyl, $C_{2-12}$-alkenyl, $C_{2-12}$-alkynyl, $C_{5-8}$-aryl, $C_{7-19}$-arylalkyl and $C_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a $C_{1-12}$-alkyl group;
or where R$^4$ and R$^5$ together with the nitrogen atom to which they are attached may form a 5- or 6-membered ring.

In a preferred embodiment of the present invention, the radicals in formula (I) have the meanings below:
$R^1$ is selected from the group consisting of methyl, ethyl, n-propyl and isopropyl,
$R^2$ is selected from the group consisting of chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoro-ethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl; 1,2,2,2-tetrafluoroethyl,
Y is selected from the group consisting of (C=O)OR$^3$, CN and (C=O)NR$^4$R$^5$, where R$^3$, R$^4$ and R$^5$ independently of one another are selected from the group consisting of methyl, ethyl, n-propyl and isopropyl.

In a particularly preferred embodiment of the present invention, the radicals in formula (I) have the meanings below:
$R^1$ is methyl,
$R^2$ is selected from the group consisting of trifluoromethyl and difluoromethyl,
Y is selected from the group consisting of (C=O)OR$^3$, where R$^3$ is methyl or ethyl.

The process according to the invention is preferably carried out in a temperature range of from −20° C. to +150° C., particularly preferably at temperatures of from −10° C. to +70° C.

The process according to the invention is generally carried out under atmospheric pressure. However, alternatively, it is also possible to operate under reduced pressure to remove the highly volatile dialkylamines.

The reaction time is not critical and may, depending on the batch size and the temperature, be chosen from a range of between a few minutes and a number of hours.

When carrying out the process according to the invention, 1 mol of the acrylic acid derivative of the formula (II) is reacted with from 0.5 mol to 3 mol, preferably from 0.5 mol to 1.5 mol, particularly preferably with an equimolar amount, of the hydrazine of the formula (III) and with from 0.5 mol to 50 mol, preferably from 0.5 mol to 20 mol, particularly preferably with from 1 to 2 mol of the compound of the formula (IV).

Preferably, the hydrazine of the formula (III), dissolved in the solvent, is initially charged together with compound of the formula (IV), and the acrylic acid derivative of the formula (II) is added. However, it is also possible to reverse the order. Ideally, the reaction is carried out directly in an excess of the compound of the formula (IV), for example in acetone or pinacolone. Prior to the isolation of the product, the acid is added to the reaction mixture. Suitable acids are selected from the group consisting of HCl, $H_2SO_4$, $CF_3COOH$, $CF_3SO_3H$, $CH_3COOH$; particular preference is given to HCl and $H_2SO_4$.

In the context of the present invention, preference is given to using 2-acylated acrylic acid derivatives of the formula (II) selected from the group consisting of ethyl (2-ethoxymethylene)-4,4-difluoromethylacetoacetate, ethyl-(2-ethoxymethylene)-4,4,4-trifluoromethylacetoacetate, ethyl-(2-ethoxymethylene)-4,4,4-trifluoromethylacetonitrile.

In the context of the present invention, the monoalkylhydrazines of the formula (III) are preferably selected from the group consisting of monomethylhydrazine, monoethylhydrazine, monopropylhydrazine and phenylhydrazine.

In the context of the present invention, the compounds of the formula (IV) are preferably carbonyl compounds; particularly preferably, they are selected from the group consisting of acetone, pinacolone, benzaldehyde, benzophenone, cyclohexanone, methyl ethyl ketone; very particular preference is given to acetone, pinacolone and benzaldehyde.

A further advantage of the process according to the invention is the fact that, to prepare the pyrazoles of the formula I, it is possible to use aqueous methylhydrazine solutions and the explosive concentrated methylhydrazine, which is also used as rocket fuel, is not necessarily required.

The reaction can be carried out in the absence of a solvent or in a solvent. The reaction is preferably carried out in a solvent. Suitable solvents are, for example, selected from the group consisting of aliphatic and aromatic hydrocarbons, such as, for example, water, alcohols (methanol, ethanol, isopropanol), n-hexane, benzene or toluene, which may be substituted by fluorine and chlorine atoms, such as methylene chloride, dichloroethane, fluorobenzene, chlorobenzene or dichlorobenzene; ethers, such as, for example, diethyl ether, diphenyl ether, methyl tert-butyl ether, isopropyl ethyl ether, dioxane, diglym, dimethylglycol, dimethoxyethane (DME) or THF; nitriles, such as methylnitrile, butylnitrile or phenylnitrile; amides, such as dimethylformamide (DMF) or N-methylpyrrolidone (NMP), or mixtures of such solvents, with acetonitrile, dichloromethane, THF, DME and ethyl acetate, acetone, water, ethanol being particularly preferred.

After the reaction has ended, for example, the solvents are removed and the product is isolated by filtration or initially extracted with water, the organic phase is separated off and the solvent is removed by distillation.

The process according to the invention is illustrated in more detail by the examples below. However, the examples are not to be interpreted as limiting.

PREPARATION EXAMPLES

Example 1

Ethyl 3-(difluoromethyl)-1-methyl-1H-pyrazole-4-carboxylate

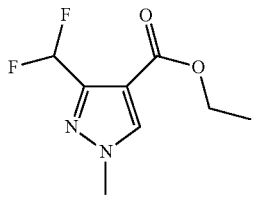

100 ml of acetone and 12 g of methylhydrazine were admixed at 10° C. and the mixture was stirred for 1 h at RT.

5.8 g (25 mmol) of ethyl 2-(ethoxymethylidene)-4,4-difluoro-3-oxobutanoate were added and the mixture was stirred at RT for 3 h, and 1 ml of 10% strength HCl was then added. GC showed only one isomer. The mixture was concentrated and the product was washed with cold water. Yield 48.3 g (94%).

$^{19}$F-NMR (CDCl$_3$): δ=−117.2 (d) ppm.
$^1$H-NMR (CDCl$_3$): δ=1.35 (t, 3H); 3.96 (s, 3H); 4.31 (kw, 2H); 7.10 (t, 1H), 8.15 (s, 1H) ppm.

Example 2

Ethyl 3-(chlorofluoromethyl)-1-methyl-1H-pyrazole-4-carboxylate

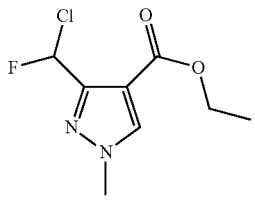

In a departure from Example 1,2-(ethoxymethylidene)-4-chloro-4,4-difluoro-3-oxobutanoate was used.

$^{19}$F-NMR (CDCl$_3$): δ=−133.8 (d, J=47.5) ppm.

The invention claimed is:

1. A process for preparing 1-alkyl-3-haloalkylpyrazole-4-carboxylic acid derivatives of the formula (I)

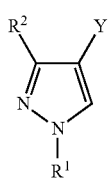

in which:
R$^1$ is selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl and C$_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a C$_{1-12}$-alkyl group;

R$^2$ is selected from C$_1$-C$_4$-alkyl groups which may be substituted by one, two or three halogen atoms selected from the group consisting of F, Cl and Br or by a CF$_3$ group;

Y is selected from the group consisting of (C=O)OR$^3$, CN and (C=O)NR$^4$R$^5$, where R$^3$, R$^4$ and R$^5$ independently of one another are selected from the group consisting of hydrogen, C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl and C$_{7-19}$-alkylaryl groups, each of which may be substituted by one or more groups selected from the group consisting of —R', —X, —OR', —SR', —NR'$_2$, —SiR'$_3$, —COOR', —(C=O)R', —CN and —CONR$_2$', where R' is hydrogen or a C$_{1-12}$-alkyl group;

or where R$^4$ and R$^5$ together with the nitrogen atom to which they are attached may form a 5- or 6-membered ring;

comprising reacting a 2-acylated acrylic acid derivative of the formula (II),

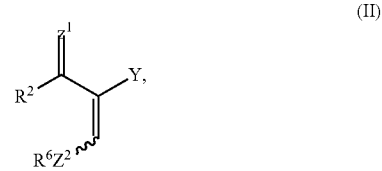

in which:
Z$^1$ and Z$^2$ independently of one another are selected from the group consisting of O and S;

R$^6$ is selected from the group consisting of C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl and C$_{7-19}$-alkylaryl groups, each of which may be substituted by one or more groups selected from the group consisting of —R', —X, —OR', —SR', —NR'$_2$, —COOR', —(C=O)R', —CN and —CONR$_2$', where R' is hydrogen or a C$_{1-12}$-alkyl group;

R$^2$ and Y have the meanings described above;
with an N-alkylhydrazine of the formula (III)

in which:
R$^1$ has the meaning described above;
in the presence of a compound of the formula (IV)

in which:
R$^7$, R$^8$ independently of one another are selected from the group consisting of H, C$_{1-12}$-alkyl, C$_{3-8}$-cycloalkyl, C$_{6-18}$-aryl, C$_{7-19}$-arylalkyl or C$_{7-19}$-alkylaryl radicals;

M is selected from the group consisting of O, S, Se, NH, and NR', where R' has the meanings defined above.

2. The process according to claim 1, characterized in that the 2-acylated acrylic acid derivative of the formula (II) is selected from the group consisting of ethyl (2-ethoxymethylene)-4,4-difluoromethylacetoacetate, ethyl-(2-ethoxymethylene)-4,4,4-trifluoromethylacetoacetate, and ethyl-(2-ethoxymethylene)-4,4,4-trifluorometbylacetonitrile.

3. The process according to claim 1, characterized in that the N-alkylhydrazine of the formula (III) is selected from the group consisting of monomethylhydrazine, monoethylhydrazine, and phenylhydrazine.

4. The process according to claim 1, characterized in that the compound of the formula (IV) is selected from the group consisting of acetone, pinacolone, benzaldehyde, and benzophenone.

5. The process according to claim 1, characterized in that the acrylic acid derivative of the formula (II) used is ethyl (2-ethoxymethylene)-4,4-difluoromethylacetoacetate, the hydrazine of the formula (III) used is methylhydrazine and the compound of the formula (IV) used is acetone.

* * * * *